(12) United States Patent
Secco et al.

(10) Patent No.: US 11,334,989 B2
(45) Date of Patent: May 17, 2022

(54) METHOD OF CLASSIFICATION AND CORRELATION BETWEEN THE PATHOLOGIC STATE OF THE SKIN AND THE CORRESPONDING THERAPY AND POSOLOGY

(71) Applicant: POLITECNICO DI TORINO, Turin (IT)

(72) Inventors: Jacopo Secco, Turin (IT); Marco Farina, Turin (IT); Fernando Corinto, Turin (IT); Danilo Demarchi, Saluzzo (IT)

(73) Assignee: Politecnico Di Torino, Turin (IT)

( * ) Notice: Subject to any disclaimer, the term of this patent is extended or adjusted under 35 U.S.C. 154(b) by 208 days.

(21) Appl. No.: 16/625,534

(22) PCT Filed: Jun. 29, 2018

(86) PCT No.: PCT/IB2018/054843
§ 371 (c)(1),
(2) Date: Dec. 20, 2019

(87) PCT Pub. No.: WO2019/021085
PCT Pub. Date: Jan. 31, 2019

(65) Prior Publication Data
US 2021/0358116 A1 Nov. 18, 2021

(30) Foreign Application Priority Data
Jul. 25, 2017 (IT) .................. 102017000084813

(51) Int. Cl.
*G06T 7/00* (2017.01)
*G16H 10/60* (2018.01)
(Continued)

(52) U.S. Cl.
CPC .......... *G06T 7/0012* (2013.01); *G16H 10/60* (2018.01); *G16H 30/40* (2018.01); *G16H 50/30* (2018.01);
(Continued)

(58) Field of Classification Search
None
See application file for complete search history.

(56) References Cited

U.S. PATENT DOCUMENTS

| 2010/0241447 A1 | 9/2010 | Siniaguine et al. |
| 2016/0210422 A9 | 7/2016 | Cellura |
| 2016/0284084 A1 | 9/2016 | Gurean et al. |

FOREIGN PATENT DOCUMENTS

WO 2015/150852 A1 10/2015

OTHER PUBLICATIONS

Sundeep Kumar K et al.: "Wound Image Analysis Classifier for Efficient Tracking of Wound Healing Status", Signal and Image Processing: An International Journal, vol. 5, No. 2, Apr. 30, 2014 (Apr. 30, 2014), pp. 15-27, XP0554741 18, In ISSN: 2229-3922, DOI: 10.5121/sipij.2014.5202 (Year: 2014).*

(Continued)

*Primary Examiner* — Vu Le
*Assistant Examiner* — Courtney Joan Nelson
(74) *Attorney, Agent, or Firm* — Workman Nydegger

(57) ABSTRACT

A system and a method of analysis of medical images of an ulcer acquired by a capturing and measuring device ($d_1, \ldots, d_N$) adapted to detect at least one parameter of the ulcer. The method provides for: —automatically and accurately identifying and classifying the ulcer and the clinical state of the ulcer being analyzed, —evaluating the evolution of the ulcer over time, —correlating the pathologic state of the ulcer detected by the capturing and measuring device ($d_1, \ldots, d_N$) with the clinical data and characteristics of the (Continued)

patient, —comparing the pathologic state of the ulcer with similar ulcers of other patients and determining a plurality of possible therapies and posologies, and —selecting, from said plurality, a therapy and a posology to be adopted for the patient in order to achieve ulcer recovery, on the basis of the success percentage of the selected therapy and posology.

15 Claims, 3 Drawing Sheets

(51) Int. Cl.
    *G16H 50/30* (2018.01)
    *G16H 50/70* (2018.01)
    *G16H 30/40* (2018.01)

(52) U.S. Cl.
    CPC ... *G16H 50/70* (2018.01); *G06T 2207/20081* (2013.01); *G06T 2207/20084* (2013.01); *G06T 2207/30088* (2013.01)

(56) References Cited

OTHER PUBLICATIONS

International Preliminary Report on Patentability dated Jan. 28, 2020, issued in PCT Application No. PCT/IB2018/054843, filed Jun. 29, 2018.
International Search Report and Written Opinion dated Sep. 13, 2018, issued in PCT Application No. PCT/IB2018/054843, filed Jun. 29, 2018.
K. Sundeep Kumar et al., *Wound Image Analysis Classifier for Efficient Tracking of Wound Healing Status*, Signal & Image Processing : An International Journal (SIPLJ), vol. 5, No. 2, Apr. 2014, pp. 15-27.
Marko Robnik-Sikonja et al., *Evaluation of Prognostic Factors and Prediction of Chronic Wound Healing Rate by Machine Learning Tools*, Jan. 1, 2003, XP055473679, pp. 25-38.
Manu Goyal et al., *DFUNet: Convolutional Neural Networks for Diabetic Foot Ulcer Classification*, Nov. 28, 2017, XP055474122, pp. 12.
Dr. James G. Spahn, *The Science of Pressure Ulcer Development, Prevention and Treatment with a View of New Approaches to Predict and Model*, Jan. 1, 2015, XP055474187, pp. 1-29.

\* cited by examiner

METHOD OF CLASSIFICATION AND CORRELATION BETWEEN THE PATHOLOGIC STATE OF THE SKIN AND THE CORRESPONDING THERAPY AND POSOLOGY

FIELD OF THE INVENTION

The present invention relates to the field of acquisition of medical images of ulcers, and more specifically to the acquisition and processing of medical images of ulcers.

More in detail, the present invention refers to techniques for classifying cutaneous ulcers in order to automatically determine the appropriate treatment, i.e. the corresponding correct therapy and posology to be applied to every single case under examination. During this process of determining the appropriate treatment, information about the patients is also taken into account.

The applicability of the present invention ranges from phlebology to dermatology, diabetology, oncology, and all fields afferent to vulnology, i.e. that branch of medicine which deals with the study of chronic lesions of the skin.

Background Art

The term cutaneous ulcer refers to a lesion or wound affecting and involving a topical area of the body, in particular the skin or the dermis, and the underlying and surrounding tissues, which is due to absent or poor blood supply to the region concerned.

A cutaneous ulcer is therefore a lesion of the skin, of the mucosae, or of the membranes covering the blood vessels, which cannot heal by itself.

For mechanical or pathological reasons, the process of re-epithelialization of a cutaneous ulcer does not occur correctly, so that the wound keeps being "alive" or active.

In the human body, ulcers may form in all cutaneous areas, but they preferably occur on the lower and upper limbs.

Unlike a common wound, such as a cut or an abrasion, an ulcer has poor, slow and reduced healing capabilities because of the insufficient blood volume being supplied to that region.

Ulcers may be due to different irritative or pathologic factors, such as, for example, diabetes. Also, continuous and prolonged pressure on a particular region of the body of people bedridden, whether permanently or for long periods of time, e.g. because of fractures, will create a decubitus ulcer or lesion. Such lesions occur in body regions that remain motionless in the same position for a long time.

Cutaneous ulcers may also arise following a physical injury, with or without vascular damage, which triggers tissue loss, infections, venous stasis, vasculitis, neoplasms, neurological problems, and autoimmune diseases with vascular involvement.

Therefore, cutaneous ulcers are a serious problem and, if the ulcer becomes infected, it will also be necessary to administer a systemic antibiotic therapy to the patient.

There are also a number of therapies that stimulate tissue regeneration, such as oxygen therapy, electrotherapy, ultrasound, and even cutaneous self-grafting, which is an invasive surgical therapy.

Of course, the treatment of cutaneous ulcers is dependent on the cause determined during the diagnosis made by the physician.

Typically, cutaneous ulcers must be treated with antiseptic solutions, compression of the region concerned with an elastic bandage, application of cicatrizant and re-epithelializing ointments.

In addition, it is also possible to use a photodynamic therapy or epithelial growth factors. It is currently a common practice to treat cutaneous ulcers with periodic medications administered by a specialist. During the examination and medication session, the physician removes the bandage, evaluates the condition of the wound, whether visually or with the aid of image acquisition devices, and, according to the circumstances, applies a new dressing or decides how the treatment should proceed.

Typically, in order to evaluate the condition of the wound it is necessary to take into account at least three essential parameters, i.e. the dimensions of the wound, the depth of the lesion and the colour of the tissues, and the variations of such parameters over time (with reference to the previous visits).

Therefore, as aforesaid, the most important characteristics that allow discerning between the healing condition and the worsening condition of a wound caused by a cutaneous ulcer are the following: extension of the wound (length and width measurements and edge evaluation), depth of the wound, and colour of the wound and of the surrounding parts.

Other characteristics or pathologic states of the patient or of the lesion are also taken into account for a correct evaluation of the condition of the ulcer.

These factors include: the infection state of the wound (typically described by an index called "infection score"), the presence and quantity of exudate, and the pain perceived by the patient.

Finally, also information about the age, race and pharmacological history of the patient and the etiology of the wound may be very important for the purpose of evaluating the treatment to be administered.

By relating all or some of the above-mentioned variable characteristics to one another, and by comparing them with the previous conditions, the specialist will be able to choose and apply the most appropriate medication for that specific case, decide if the ulcer has reached a necrotic condition (which will lead, in most cases, to surgical removal of the necrotized piece of tissue or, in the most serious cases, to amputation of the entire limb), and possibly prescribe a pharmacological treatment in addition to dressing.

Notwithstanding its proven curative effectiveness, this sequence of steps implies much discomfort for the patients, who are compelled to move in order to reach the treatment sites in spite of the pain they are suffering, and all the problems that may ensue from such circumstances (including a high risk of contracting infections).

In general, however, the physician encounters much difficulty in prescribing the correct posology without the aid of systems capable of relating all the above-mentioned data to one another and analyzing them with precision and uniformity.

This problem increases the treatment time, and may also lead to a possible drastic worsening of the clinical conditions of the patient, should the prescribed treatment not be the most appropriate one.

Several prior-art patent documents are known:

US20160210422, "System and methods of obtaining reimbursements for patient treatment", US20100241447, "Customization of wound dressing using rule-based algorithm", WO2015150852, "Automatic determination of appropriate medical products according to wound classification", ITUB201595960, "Device and method of acquisition of medical images for ulcer analysis".

Several publications are also available which deal with this problem:
1. LeCun, Yann, Yoshua Bengio, and Geoffrey Hinton, "Deep learning", Nature521.7553 (2015): 436-444;
2. Secco, Jacopo, et al., "Memristor cellular automata through belief propagation inspired algorithm", 2015 International SoC Design Conference (ISOCC). IEEE, 2015;
3. Secco, Jacopo, et al., "Memristor cellular automata for image pattern recognition and clinical applications", Circuits and Systems (ISCAS), 2016 IEEE International Symposium on. IEEE, 2016;
4. Roska, Tamas, and Joos Vandewalle, "Cellular neural networks", Cellular neural networks (1993);
5. Chua, Leon O., and Lin Yang., "Cellular neural networks: Applications", IEEE Transactions on circuits and systems 35.10 (1988): 1273-1290;
6. Ricci, Elia, Roberto Cassino, and Mario Nano, "Piaghe da decubito", *Minerva medica,* 2004.

However, none of such documents provides a solution to this problem.

OBJECT AND SUMMARY

There is a need for determining a correct therapy and posology for each case under examination, so as to facilitate and speed up the healing of the ulcer.

There is also a need for avoiding useless and detrimental trips of the patients to the places of treatment of their ulcers, unless strictly necessary, e.g. for more invasive treatments. It is therefore the object of the present invention to propose a system capable of carrying out a process of analysis of images and clinical data of ulcers, which allows for automatically and accurately identifying and classifying the ulcers and the clinical state of an ulcer, as well as evaluating the evolution thereof over time, for the purpose of determining the most appropriate therapy.

In particular, the aim is to correlate the pathologic condition of the skin and/or dermis, detected by the capturing and measuring device(s), and the characteristics of the individual patient with a corresponding therapy and posology necessary for recovery.

Some embodiments of the present invention relate to a system and a method adapted to process ulcer data and capable of correlating them with the characteristics of individual patients through predictive and evolutionary algorithms, for the purpose of accurately establishing the best posology for the case under examination, thereby considerably reducing the time of treatment and making the procedure more efficient.

This invention is an autonomous and automatic tool useful as a support for the physician, regardless of the type of device used by the latter for processing the data received from the family doctor, which allows for quick ulcer classification and which can autonomously determine the most appropriate treatment on the basis of a plurality of cases stored in a database, which is constantly updated with newly analyzed cases.

The method described herein can improve its own precision of computation as the amount of data available on a common platform increases. The data are automatically correlated at every interaction, and the method is able to attribute weights to the various values available, thus accurately defining which data are most relevant and which data are least relevant for the individual case under examination.

BRIEF DESCRIPTION OF THE DRAWINGS

Further features and advantages of the invention will become apparent in the light of the following detailed description, which is provided merely by way of non-limiting example with reference to the annexed drawings, wherein.

DETAILED DESCRIPTION

The following description will illustrate various specific details useful for a deep understanding of some examples of one or more embodiments. The embodiments may be implemented without one or more of such specific details or with other methods, components, materials, etc. In other cases, some known structures, materials or operations will not be shown or described in detail in order to avoid overshadowing various aspects of the embodiments. Any reference to "an embodiment" in this description will indicate that a particular configuration, structure or feature described in regard to an embodiment is comprised in at least one embodiment. Therefore, the phrase "in an embodiment" and other similar phrases, which may be present in different parts of this description, will not necessarily be all related to the same embodiment.

Furthermore, any particular configuration, structure or feature may be combined in one or more embodiments as deemed appropriate.

The references below are therefore used only for simplicity's sake, and do not limit the protection scope or extension of the various embodiments.

The invention described herein provides an aid for a physician dealing with pathologic skin cases, such as melanomas, ulcers, sclerodermas and eschars, which need long follow-up and therapy periods to recover.

Figure 1:
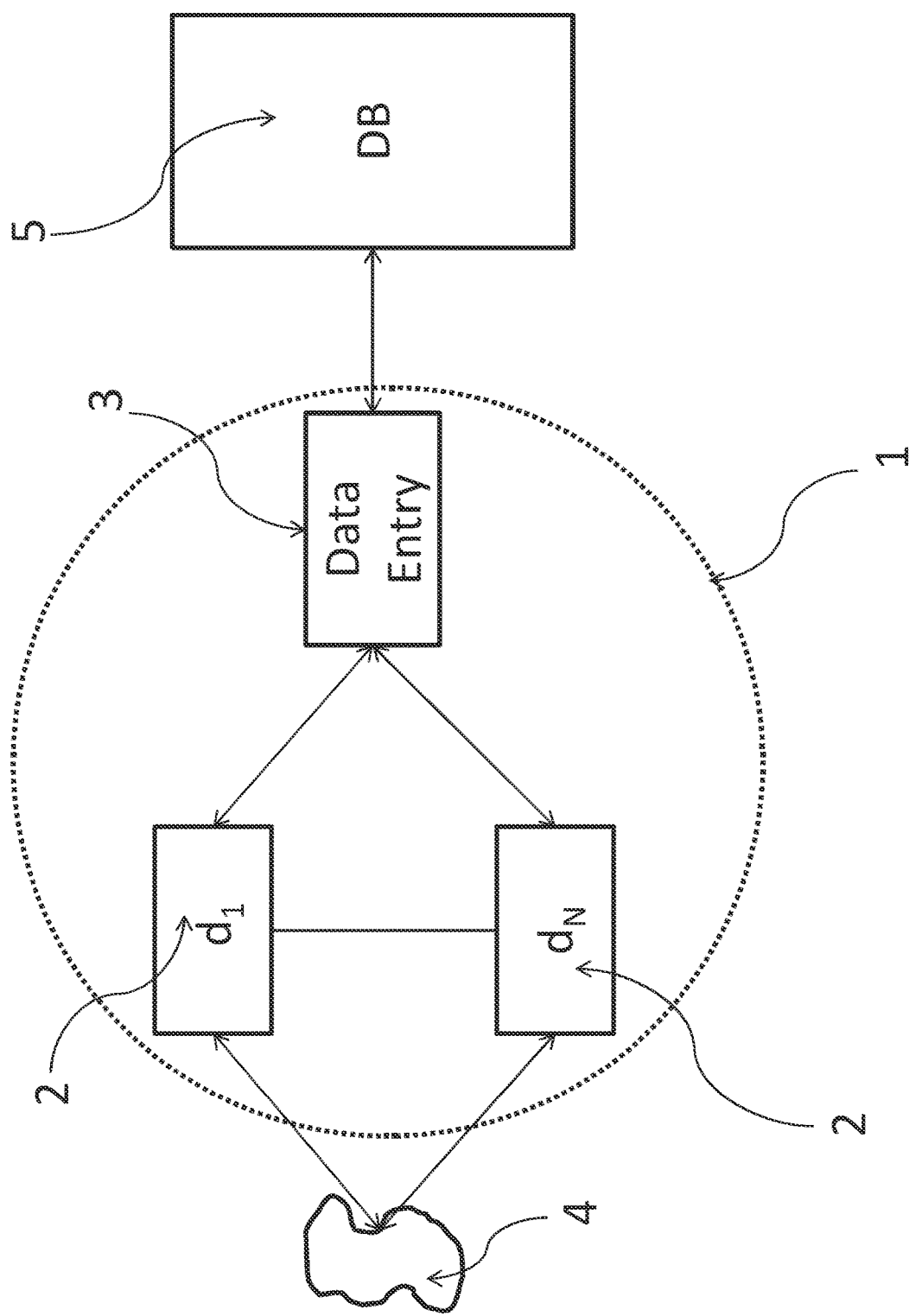
FIG. 1 shows an example of a first configuration of the system.

FIG. 1 shows a first configuration of the system according to the invention. FIG. 1 illustrates the terminal, designated as a whole by reference 1, made up of one to N systems, devices or methods for measuring the parameters of the ulcer (dimensions, depth, colour), each one designated by reference 2, connected to a data entry device, designated by reference 3.

The measuring systems 2 are adapted to measure the necessary parameters of the lesion, designated by reference 4.

These measured parameters are then entered into a database 5 by means of the data entry device 3, which is connected, over the Internet network, to the remote database 5. The connection can be established by any means allowed by the same data entry device 3, e.g. Wi-Fi, Ethernet network, Bluetooth or the like.

Figure 2:
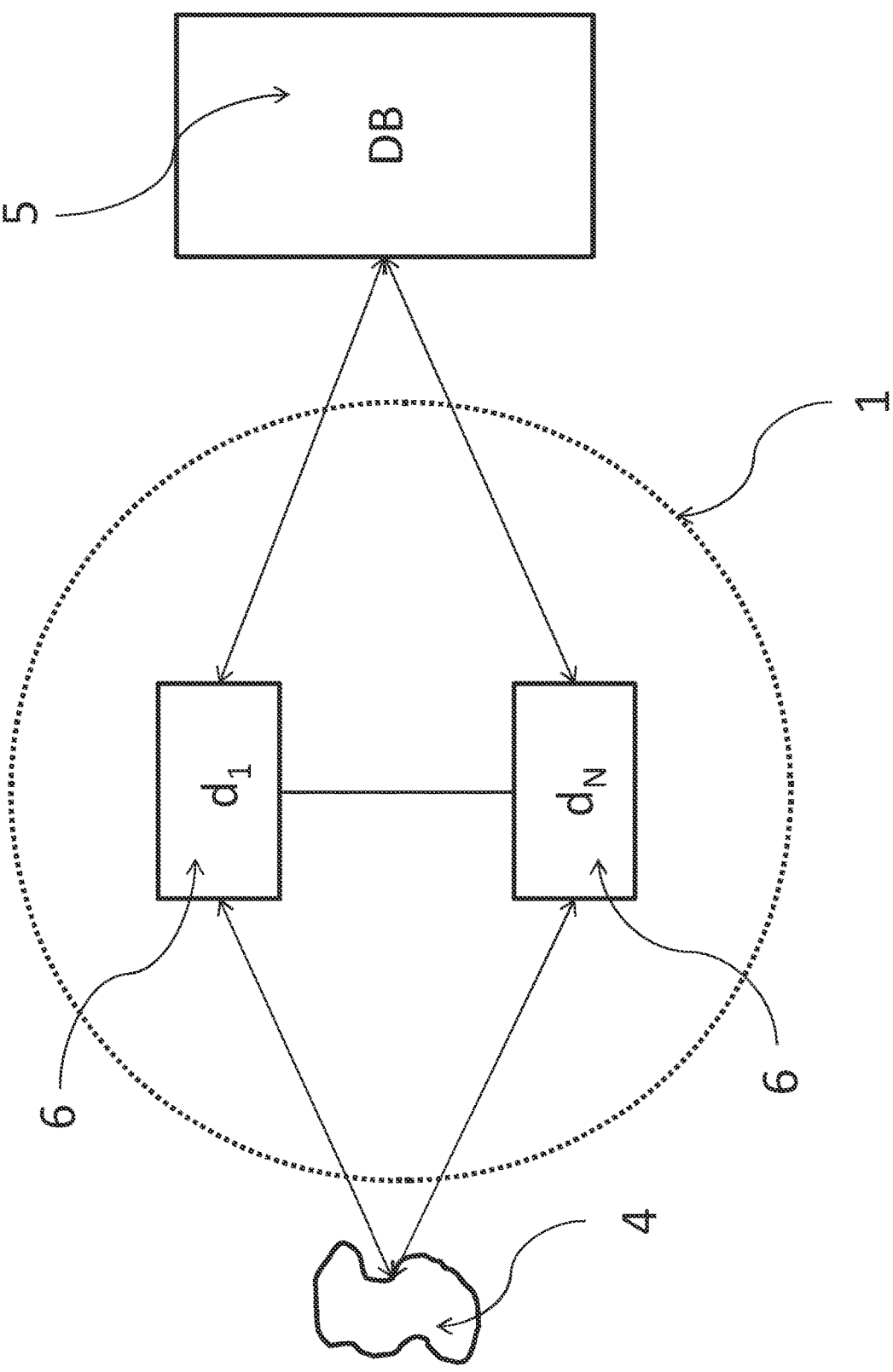
FIG. 2 shows an example of a second configuration of the system.

FIG. 2 shows a second possible configuration of the system. FIG. 2 illustrates the terminal designated as a whole by reference 1, made up one or more devices, methods or systems of measurement, designated by reference 6, directly connected to the database 5 over the Internet network and by any means allowed by the device, e.g. Wi-Fi, Ethernet network, Bluetooth or the like.

In this case, the measuring systems 6 allow for direct connection to the database 5, and the measured parameters and the clinical data are entered either automatically, by a suitable application, or manually, via a data entry interface.

Figure 3:
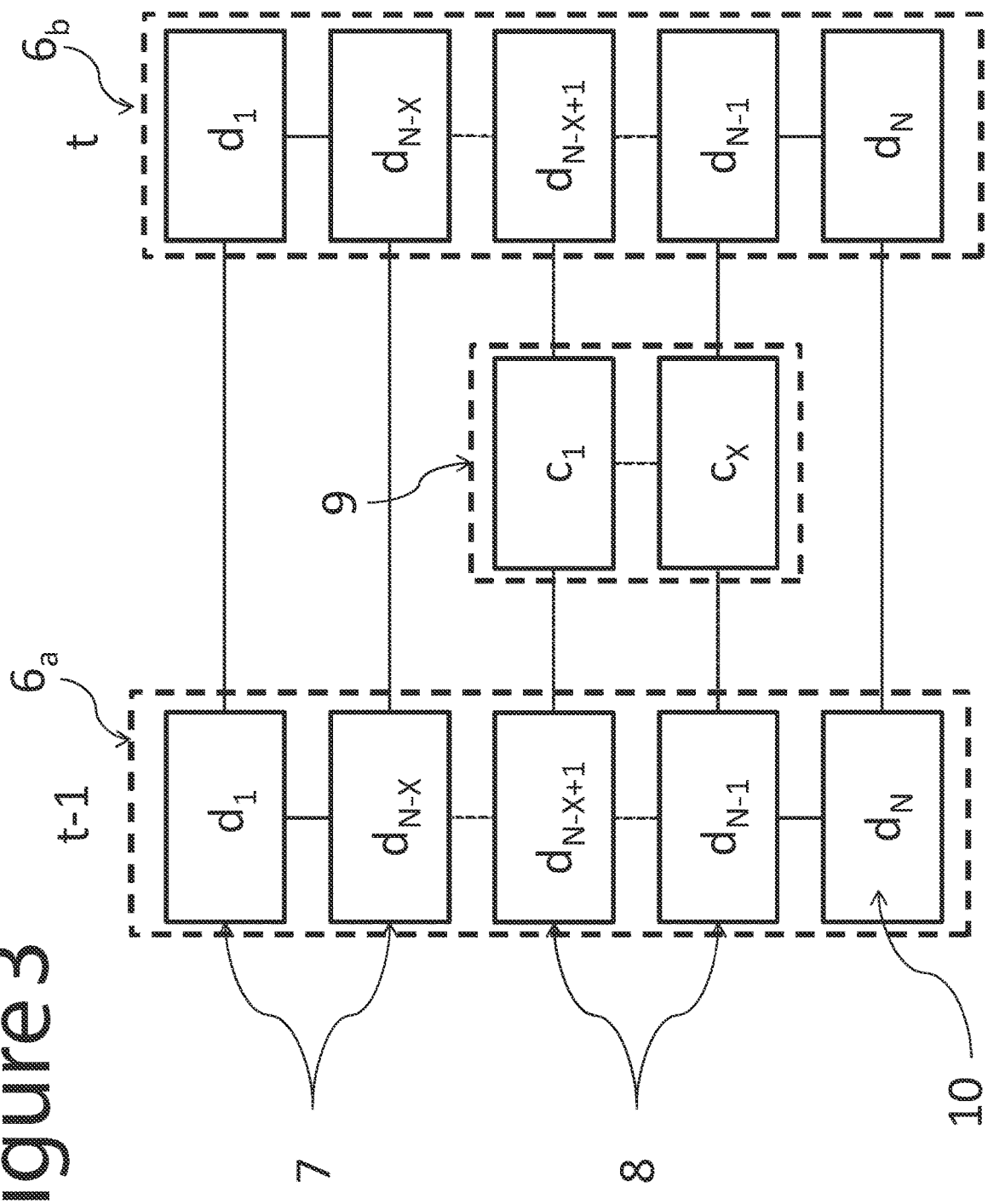
FIG. 3 shows the structure of the clinical data relating to a single patient.

FIG. 3 shows the structure of the parameters relating to a single patient's case.

The data about the visit conducted, designated as a whole by reference $6_b$, are related to those concerning the previous visit, designated by reference $6_a$. The non-evolutionary data or parameters, designated in the drawing by reference 7, remain the same at every visit (first name, surname, sex, race, skin type, etc.).

The evolutionary parameters, designated in FIG. 3 by reference 8, are normally numerical data subject to change over time (ulcer dimensions) and are connected through variation indices ($c_1, \ldots, c_X$), designated in FIG. 3 by reference 9, computed as the differences in the values of the corresponding evolutionary parameters at the time "t" and at the time of the previous visit "t−1".

The parameter concerning the applied posology is designated in FIG. 3 by reference "$d_N$" and varies for manual or automatic entry depending on the adopted configuration, i.e. that of FIG. 1 or that of FIG. 2.

The invention is based on three main elements:

1) a terminal 1 for analyzing and entering data relating to the patient's cutaneous pathology (e.g. three-dimensional dimensions of the ulcer or wound colour), as well as any prescribed therapy and posology, into the corresponding clinical record of the patient;

2) a database 5 for collecting the clinical records from all terminals 1; and 3) an algorithm allowing the creation of a correlation between the data relating to the cutaneous pathology of the patient under observation, the therapy that has been administered by the doctor, and the progress of recovery.

The terminal 1 can also be described as a generic system for acquiring parameters ($d_1, \ldots, d_N$) relating to the cutaneous pathology and the administered therapy (such as, for example, Wound Viewer technology or the like).

The terminal 1 may be a device or a system capable of entering, either manually or automatically, all the above-mentioned data (evolutionary and non-evolutionary parameters).

The terminal designated by reference 1 may also be composed of several elements: at least one for measuring the parameters, designated by reference 2, and one for entering the data into the record, designated by reference 3.

In case the measuring devices 2 are other than the data entry device 3 (first configuration 1 shown in FIG. 1), they may be one or more evaluation devices, methods or systems 2 adapted to provide measurements as accurate as possible of the morphological parameters of the lesion 4 and of the degree of infection, e.g. as described in, without being limited to, the above-mentioned patent ITUB201595960, "Device and method of acquisition of medical images for ulcer analysis".

The data entry device 3 may be any device connected to the network and allowing the parameters measured by the measuring device 2 to be transferred the database 5.

Data transfer may be effected manually, in the absence of a direct connection between the measuring device 2 and the data entry device 3; in such a case, the data entry device 3 may be a tablet, a smartphone or a (laptop or desktop) computer, or other similar devices, on condition that it is connected to the network for updating the remote database 5 with new data.

Both the measuring device 2 and the data entry device 3 must comprise the interface necessary to allow a proper evaluation of the measurement and the correct entry of the data, such as, by way of non-limiting example, a physical or virtual keyboard and a screen.

The data entry device may also be the measuring device itself, designated as a whole in FIG. 2 by reference 6, if the latter allows a network connection, and hence direct or manual entry of data into the record, and then into the database 5, either via a suitable application or manually by means of a data entry interface (second configuration shown in FIG. 2).

Such data are entered into the patient's clinical record at each visit, thus making it possible to follow and monitor the variation of all parameters of interest over time. The evolutionary parameters entered ($d_1, \ldots, d_N$), with their respective relationships, are listed below along with the indication of the value to be entered:

1. Patient Profile (text)
   a. First Name and Surname (text)
   b. Age (number)
   c. Ethnic Group (text)
   d. Sex (text)
   e. Anamnesis (text)
   f. Lesion (coded identification number)
   i. Visit date (number)
   [1] Extension (number)
   [2] Depth (number)
   [3] Etiology (text)
   [4] Granulation (number)
   [5] Wound Bed Preparation Score (alphanumeric code)
   [6] Infection Score (number)
   [7] Pain Scale (number)
   [8] Applied Therapy and Posology (text)

The data represented herein (evolutionary parameters and fixed parameters) are considered to be fundamental for a correct evaluation of the best posology, but they may be integrated with additional data (concerning the patient or the lesion) in order to further improve the effectiveness of the evaluation.

For the purposes of the present description, the parameter relating to the applied therapy and posology will be indicated as parameter $d_N$.

As described above, the data entered are related at multiple levels in order to allow the system to recognize the correct correlation between a single patient and his/her general clinical conditions and the conditions of his/her lesions.

The output data of the system are the following:
1. Recommended therapy and posology (text)
2. Success percentage (number)
3. Actual area amelioration (number)
4. Actual volume amelioration (number)
5. Actual depth amelioration (number)
6. Actual granulation amelioration (number).

The database 5 is connected to the various terminals 1 through the Internet network, and its function is to store all the patients' clinical records, including the data concerning the prescribed posologies.

The actual connection between the database DB 5 and the data entry device 3 or 6 (in the first or second configuration) depends on the device used for data entry and its connection method.

The connection can be established by any means capable of connecting to the Internet network, whether wireless (e.g.

Wi-Fi or Bluetooth, without however being limited thereto) or wired (e.g. Ethernet, without however being limited thereto).

The database 5 is implemented on a suitable server, whereon the algorithm for studying the correlation among the data resides.

The algorithm is a cellular neural network (CNN) having "machine learning" properties, i.e. the capability of dynamically adapting itself to newly entered data.

Cellular neural networks (CNN) consist of an array of non-linear dynamic processors/circuits interacting together via programmable connections.

The input applied to the entire array is typically mapped on a two-dimensional topographic structure (e.g. images, arrays of electrodes or sensors, etc.).

In this specific case, the input data correspond to the data that the measuring devices 1 have entered, whether manually or automatically, into the respective clinical records of the patients. This will depend on the type of device in use, i.e. whether it is a device with separate measuring elements 2 and data entry elements 3 or a device 6 integrating both features into a single element.

CNN cellular neural algorithms are based on a structure of mutually connected cells that change their own "weights" when processing a decision.

The term "weight" refers to the computational and statistical importance associated with every single datum. The algorithm described herein allows defining a statistic or providing an output on the basis of the analysis of input information.

The statistic under examination refers to the best posology applicable, correlated with its success percentage.

The term "success percentage" refers to the number of cases in which patients with characteristics and wounds similar to those of the patient under examination have shown an improvement with the recommended therapy.

Said percentage is also correlated with the actual amelioration, to be understood as the positive variation of the clinical condition of the wound in terms of area, volume, depth and granulation.

These weights vary as new input data are entered, and the neural network will iteratively calibrate the correct value of the weights of such data so as to increasingly optimize the output datum.

The complexity of CNN neural networks and the interfacing method thereof may vary extensively according to the complexity of the response that they are expected to provide as output.

For example, it is possible to design networks formed by several planar layers of cells, wherein the layers are connected to each other through one or more nodes.

This "multi-layer" technique is referred to as "deep learning", and allows the completion of very complex processing of a very large number of values at low computational costs.

The input parameters $(d_1, \ldots, d_N)$ represent the nodes of the first data layer. Each node is associated with "t" different layers formed by "twin" nodes similar to the first ones, which represent the evolution of the same parameters over time. The parameter "t" indicates the temporality of parameter collection.

Therefore, each layer has the same dimensions as the first layer, and each one represents a new input of each parameter corresponding to every new check or examination made by the doctor.

Some parameters will be evolutionary (those concerning the morphology of the lesion, the degree of infection, the level of perceived pain), while others will be fixed (e.g. those concerning the patient's personal data).

Between the nodes $d^t$ and the next node $d^{t+1}$ (where t is the point in time when examination took place) of the evolutionary numeric parameters (in a number x for each patient), there is a connection node "c" that represents the index of variation or evolution of the individual parameter. The values of the evolution indices $(c_1, \ldots, c_X)$ for each visit will establish the differences between the values $d_N$ relating to the posology.

In addition to being connected to the administered therapy, the latter will also be connected to some personal data of the patient, such as sex and ethnic group, which may affect, as will be further explained hereinafter, the patient's recovery progress.

The continuous evolution of the neural network creates a series of weight vectors associated with all the parameters d and with the variation indices c; therefore, for each patient a series of weights $P=(p_1, \ldots p_{N+X})$ will be processed.

These weights are from time to time compared with the case of the patient under examination. The high computational efficiency of the network is due to the fact that only those weights which are relevant for the case under examination will be taken into account for processing.

The constant addition of parameters and data into the database 5 allows increasing the software's data correlation capability, thanks to machine learning algorithms.

In particular, extraction and updating of the information useful for treating the patients (through the selection of the correct therapy and posology) occur through the following steps:

pre-processing the information described in the "visit data" (the above parameters $(d_1, \ldots, d_N)$), based on biunivocal transformations that provide a representation useful for training the non-linear network with local connections (Cellular Non-linear Network—CNN). The differences in the evolutionary parameters between the current view and the previous view will provide the evolution indices $(c_1, \ldots, c_X)$, determining the "weights of the local interconnections" $(p_1, \ldots p_{N+X})$ on the basis of the correlation between the parameters d and the evolution indices c, the treatment prescribed by the physician, and the course of the wound, evaluated by the physician, predicting the evolution of the pathologies and updating the database.

The weights are determined as follows, considering a database 5 including N cases (i.e. N patients).

1. Among the N cases, those cases $N_p$ are counted which have shown a positive evolution of the wound (meaning by positive evolution a change in the evolutionary data of the wound that indicates a clinical amelioration thereof, such as reduced area, volume, depth and granulation), 2. For each one of the Np cases, the data relating to the applied posology $d_N$, are extracted, 3. Those cases with the same datum $d_N$ of therapy and posology are grouped together; therefore, for each $d_N$ taken into consideration, there will be K positive cases with the same applied posology, 4. For each one of the K cases of each extracted $d_N$:
  a. The single weights P relating to the evolutionary parameters d (all except the applied posology $d_N$), i.e. $(p_1, \ldots, p_{N-1})$ (initialized at value 0 when first entered) are incremented by one unit if the evolutionary parameters of the patient under examination and the data d of the comparison case match, b. The single weights ($p_{N+1}, \ldots p_{N+X}$) relating to the connection indices c are computed by considering the connection indices c of the comparison case as:

$$p_i = \frac{c_i}{d_i^{z-1}} * (-1),$$

c. The weight of the applied posology $d_N$ is computed as $p_{d_N} = (\Sigma_{n+x-1}^{i=1} p_i)/K$ 5. The recommended posology is the one with the highest weight $p_{d_N}$.

6. The success percentage is $p_{d_N}$.

7. The amelioration rate is given by the arithmetic mean, among the various K cases of the selected $d_N$, of the data c relating to area, volume, depth and granulation.

Cutaneous pathologies (melanomas, ulcers, sclerodermas, eschars, etc.) can be either acute or chronic.

Often the chronic state derives from an improper treatment of the pathology, which was initially of an acute nature.

In light of this criticality, it is necessary to provide the physician with tools allowing a high frequency of follow-up checks of the patient's condition, so that the physician will be able to administer and prescribe the most appropriate therapy and rapidly evaluate whether the prescribed therapy is leading to recovery or worsening of the ulcer.

In the specific case of cutaneous ulcers, inadequate follow-up may lead to amputation of the limb where the ulcer has formed or, for melanomas, to death of the patient.

From accredited sources (Associazione Italiana Ulcere Cutanee, AIUC, and Istituto Europeo Oncologico, IEO) it is known that in 70% of cases the posology for the disease shows some incongruities in relation to the patient to whom the treatment is being administered.

It has been scientifically demonstrated that the curative path is strongly dependent on a number of factors related to the patient, such as, for example, his/her sex, race or anamnesis.

Certain races or ethnic groups react differently to many active principles. This is also due, as far as dermatologic disorders or syndromes are concerned, to the different characteristics of the skin.

The same principle applies to the age and sex of the patient, which lead to different general characteristics of the epithelium and dermis.

In addition to the above-mentioned characteristics, also the anamnesis, the etiology of the lesion and the other characteristics of the lesion play a role in the decision of the correct posology.

At present no method is available which can establish the most appropriate posology on the basis of previously studied cases.

In this respect, specialist physicians encounter much difficulty in determining the appropriate treatment on the basis of all the parameters that need to be taken into account.

Through the method mentioned and described above, it is possible to relate the most appropriate treatment to the pathology under examination, due to a number of clinical cases stored in the database, which can be defined as potentially infinite, so that accurate statistics can be established about the potentiality of a given treatment for a specific case. Thanks to CNN neural networks and their use in the biomedical field, it is possible to establish, due to a multitude of data available, the characteristics of the single patient which have a relevant weight in the decision. This is done by the CNN, which can understand, thanks to the available statistics, the most relevant data at every new addition of values.

The method allows screening the existing cases and the history of such cases to automatically create a matching between the treatments administered by the physicians and the progress of recovery from the pathology.

The doctor preserves a key role in prescribing the treatment, but at the same time he/she can utilize a decision support system capable of showing, based on a considerable history of clinical data, which treatment would be the best for the specific clinical pathology of the specific case under examination.

The data returned by the system are presented to the physician as a report. The physician will have the possibility of consulting the report through the data entry system or device 1, connected to the database 5 over the network in its various configurations.

Based on the characteristics of the patient under analysis, correlated with those cases which are most similar thereto, statistics can be processed by relating the state of the wound to the possible posologies, thus obtaining an expected degree of effectiveness.

The doctor can thus utilize this report to determine the most appropriate treatment for his patient, by accurately establishing, even in the absence of a large number of data about that single patient, a treatment strategy that will be most appropriate and compliant with the requirements of the case under examination by using information about similar patients.

As previously described, cellular neural networks (CNN) are a powerful means for the analysis of data when the latter become "massive". In fact, cellular neural networks (CNN) are considered to be the best form of management within the "Big Data" sphere.

The innovation provided by the invention is represented by two main factors:

1) the capability of implementing CNN networks within a biomedical application requiring high computation power for the desired purpose;

2) the ability of the system to evaluate in real time the effectiveness of a given therapy and posology for the case under examination.

The use of a CNN network allows for effective processing in real time of a great amount of data, while automatically including, as explained in the previous description of the computational method, the characteristics and the data of the individual patients that most affect the decision of the appropriate therapy and posology on the basis of previously obtained results stored in the database.

The structure of the CNN network relates the data of the single patient and their evolution over time, correlating them with previously obtained curative results.

By making this computation for each patient, it is possible to segment the data population of the DB into classes, putting the individual cases in relation with other similar cases or with cases having similar characteristics.

In this manner, the CNN network has the possibility of changing the weights of the single data in order to mathematically comprise the relevance thereof into the result obtained.

After a thorough evaluation of the literature, it can be stated that no predefined scheme for therapy selection exists.

As previously described, in most cases (70%) the selected therapy and posology do not turn out to be the most adequate ones.

This problem is generated by the presence of a number of "hidden" variables that make it difficult for the physician to find out the most suitable therapy. Such variables may be related to the patient's characteristics, such as race, sex and age, or to his/her anamnesis or lesion type.

Each one of these variables has a relevance weight in the determination of the most effective curative path. In the absence of adequate computation systems like the one illustrated in the present patent, it is extremely difficult for the physician to establish these relationships with accuracy, also because of the lack of data concerning the plurality of clinical and literature cases. It is a task of the system presented herein to fill this gap by providing the physician with such a computational tool.

The purpose of CNN algorithms is to find the hidden variables in a given problem and formulate a standardized practice based on experience and extrapolated statistics.

The exploitation of the "machine learning" and evolutionary properties of these systems should be considered as fundamental. Existing technologies are based on static and complex decision algorithms. The dynamism of this system makes it capable of evolving every time an operator enters new data.

Unlike the methods currently under development (according to priority searches carried out), the one of the present application has a high degree of automation.

The methods described in the patents found during the priority analysis are based on static procedures that give little importance to the characteristics of the single patient. Studies carried out have shown that the singularity of each patient is fundamental in order to formulate an adequate diagnosis or posology.

Such cases are extremely frequent and constantly evolving. The proposed algorithm solves this problem by taking into consideration new cases and by adapting itself dynamically thereto.

The existing technologies allow establishing a posology with an error of 70%. Through this system it is possible to considerably reduce the error proportionally to the number of cases stored and registered in the system.

Current systems interface to large databases with slow response times. Conversely, through CNN algorithms it is possible to attain the same results while halving the computation and association times.

Of course, without prejudice to the principle of the invention, the forms of embodiment and the implementation details may be extensively varied from those described and illustrated herein merely by way of non-limiting example, without however departing from the protection scope of the present invention as set out in the appended claims.

The invention claimed is:

1. A method of analysis of medical images of an ulcer of a patient acquired by a capturing and measuring device adapted to detect at least one parameter of said ulcer at each visit of the patient, wherein said method provides for:
automatically and accurately identifying and classifying the ulcer based on the clinical state of the ulcer being analyzed,
evaluating the evolution of the ulcer over time,
correlating the pathologic state of the ulcer detected by said capturing and measuring device with the clinical data and characteristics of the patient,
comparing the pathologic state of the ulcer with similar ulcers of other patients and determining a plurality of possible therapies and posologies, and
selecting, from said plurality, a therapy and a posology to be adopted for the patient in order to achieve ulcer recovery, on the basis of the success percentage of the selected therapy and posology,
wherein the therapy and posology are selected by means of a cellular neural network (CNN) having "machine learning" properties that allow it to dynamically adapt itself according to the new data entered at each visit of the patient.

2. The method according to claim 1, wherein parameters which are measured and stored at each visit are the so-called evolutionary parameters and comprise:
Visit date (number),
Ulcer extension (number),
Ulcer depth (number),
Etiology (text),
Granulation (number),
Wound Bed Preparation Score (alphanumeric code),
Infection Score (number),
Pain Scale (number), and
Applied posology (text).

3. The method according to claim 2, wherein the evolutionary parameters measured at each visit are correlated with the values of the same parameters acquired during the previous visits, and evolution indices ($c_1, \ldots, c_X$) are created which define the differences over time among the values of the measured evolutionary parameters and which are correlated with the administered therapy and posology.

4. The method according to claim 3, wherein the continuous evolution of the neural network creates a series of weights ($p_1, \ldots, p_{N+X}$) associated with all measured parameters and evolutionary indices ($c_1, \ldots, c_X$), and said weights ($p_1, \ldots, p_{N+X}$) are from time to time compared with the case under examination, and only those weights which are relevant for the case under examination are taken into account for processing and selecting the therapy and posology to be administered to the patient.

5. The method according to claim 4, wherein the information useful for selecting the therapy and posology to be administered to the patient is extracted and updated through the following steps:
pre-processing of the measured evolutionary parameters based on biunivocal transformations that provide a representation useful for training the non-linear network with local connections,
computing the difference in the evolutionary parameters between the current visit and the previous one, and defining the variation indices ($c_1, \ldots, c_X$),
determining the "weights of the local interconnections" ($p_1, \ldots, p_{N+X}$) on the basis of the correlation between the evolutionary and non-evolutionary parameters and the evolution indices ($c_1, \ldots, c_X$), the prescribed therapy and posology, and the course of the ulcer, and
predicting the evolution of the pathologies and updating the data.

6. The method according to claim 5, wherein the weights ($p_1, \ldots, p_{N+X}$) are determined through the following steps:
among the N cases, those cases $N_p$ which have shown a positive evolution of the ulcer are counted,
for each one of the Np cases, the data relating to the applied posology ($d_N$) are extracted,
those cases which have the same posology datum (dN) are grouped together; therefore, for each posology ($d_N$) taken into consideration there will be K positive cases with the same applied posology,
for each one of the K cases of each extracted posology ($d_N$):
the single weights ($p_1, \ldots, p_{N+X}$) relating to the evolutionary parameters, except the applied posology ($p_1, \ldots, p_{N-1}$), are incremented by one unit if the evolutionary parameters of the patient under examination and the evolutionary parameters of the comparison case match, the single weights ($p_{N+1}, \ldots, p_{N+X}$) relating to the evolution indices ($c_1, \ldots, c_X$) are computed by considering the variation indices ($c_i$) of the comparison case as:

$$p_i = \frac{c_i}{d_i^{t-1}} *(-1),$$

the weight of the applied posology ($d_N$) is computed as $p_{d_N} = (\Sigma_{n+x-1}^{i=1} p_i)/K$, the recommended posology ($d_N$) is the one with the highest weight $p_{d_N}$, the success percentage is $p_{d_N}$, the amelioration rate is given by the arithmetic mean, among the various K cases of the selected posology ($d_N$), of the evolution indices ($c_1, \ldots, c_X$) relating to area, volume, depth and granulation.

7. The method according to claim 6, wherein said method allows screening the existing cases and the history of such cases, thus automatically creating a matching between the treatments administered to the patients in each case and the progress of recovery from the disease.

8. The method according to claim 1, wherein the clinical data and characteristics of the patient are the fixed parameters that are stored in a clinical record and comprise:
Patient Profile (text),
First Name and Surname (text),
Age (number),
Ethnic Group (text),
Sex (text),
Anamnesis (text),
Lesion (coded identification number).

9. The method according to claim 1, wherein the following parameters are updated at each visit:
Recommended posology (text),
Success percentage (number),
Actual area amelioration (number),
Actual volume amelioration (number),
Actual depth amelioration (number),
Actual granulation amelioration (number).

10. The method according to claim 1, wherein the processing of the data relating to the ulcer allows for fast classification of the ulcer and autonomous determination of the therapy and posology on the basis of a plurality of cases stored in a database containing the data relating to all the analyzed cases.

11. The method according to claim 1, wherein said method has the capability of improving its computation precision as the amount of available data increases, wherein the data are correlated automatically at every iteration.

12. A terminal for autonomously determining the therapy and posology to be applied for treating an ulcer, adapted to carry out the method according to claim 1.

13. A system for autonomously determining the therapy and posology to be applied for treating an ulcer, comprising:
at least one terminal according to claim 12, for analyzing, acquiring and entering data relating to the cutaneous pathology suffered by the patient, as well as the therapy and posology possibly prescribed in the corresponding clinical report of the patient;
a database for collecting the clinical reports coming from said at least one terminal; and
a method of data analysis, which allows making a correlation between the data relating to the cutaneous pathology, the administered therapy, and the progress of recovery.

14. A computer program product loaded into non-transitory memory of a digital processing device and which comprises portions of software code for executing the method according to claim 1.

15. A method of analysis of medical images of an ulcer of a patient acquired by a capturing and measuring device adapted to detect at least one parameter of said ulcer at each visit of the patient, wherein said method provides for:
automatically and accurately identifying and classifying the ulcer based on the clinical state of the ulcer being analyzed,
evaluating the evolution of the ulcer over time,
correlating the pathologic state of the ulcer detected by said capturing and measuring device with the clinical data and characteristics of the patient,
comparing the pathologic state of the ulcer with similar ulcers of other patients and determining a plurality of possible therapies and posologies, and
selecting, from said plurality, a therapy and a posology to be adopted for the patient in order to achieve ulcer recovery, on the basis of the success percentage of the selected therapy and posology,
wherein parameters which are measured and stored at each visit are the so-called evolutionary parameters and comprise:
Visit date (number),
Ulcer extension (number),
Ulcer depth (number),
Etiology (text),
Granulation (number),
Wound Bed Preparation Score (alphanumeric code),
Infection Score (number),
Pain Scale (number), and
Applied posology (text),
wherein the evolutionary parameters measured at each visit are correlated with the values of the same parameters acquired during the previous visits, and evolution indices ($c_1, \ldots, c_X$) are created which define the differences over time among the values of the measured evolutionary parameters, and which are correlated with the administered therapy and posology,
wherein the continuous evolution of the neural network creates a series of weights ($p_1, \ldots, p_{N+X}$) associated with all measured parameters and evolutionary indices ($c_1, \ldots, c_X$), and said weights ($p_1, \ldots, p_{N+X}$) are from time to time compared with the case under examination, and only those weights which are relevant for the case under examination are taken into account for processing and selecting the therapy and posology to be administered to the patient.

* * * * *